(12) United States Patent
Goldfine et al.

(10) Patent No.: US 7,095,224 B2
(45) Date of Patent: Aug. 22, 2006

(54) PROCESS CONTROL AND DAMAGE MONITORING

(75) Inventors: Neil J. Goldfine, Newton, MA (US); Darrell E. Schlicker, Watertown, MA (US); Andrew P. Washabaugh, Chula Vista, CA (US); David C. Grundy, Reading, MA (US); Vladimir A. Zilberstein, Chestnut Hill, MA (US)

(73) Assignee: Jentek Sensors, Inc., Waltham, MA (US)

( * ) Notice: Subject to any disclaimer, the term of this patent is extended or adjusted under 35 U.S.C. 154(b) by 0 days.

(21) Appl. No.: 10/762,193

(22) Filed: Jan. 21, 2004

(65) Prior Publication Data

US 2004/0174157 A1 Sep. 9, 2004

Related U.S. Application Data

(60) Provisional application No. 60/441,691, filed on Jan. 21, 2003.

(51) Int. Cl.
 *G01R 33/12* (2006.01)
 *G01B 7/00* (2006.01)
 *G01N 27/72* (2006.01)

(52) U.S. Cl. ...................... 324/228; 324/244

(58) Field of Classification Search ........ 324/228–230, 324/232, 234–243, 207.13, 207.15–207.24, 324/244, 323, 326, 331
 See application file for complete search history.

(56) References Cited

U.S. PATENT DOCUMENTS

| 4,814,690 | A | 3/1989 | Melcher et al. |
| 5,015,951 | A | 5/1991 | Melcher |
| 5,453,689 | A | 9/1995 | Goldfine et al. |
| 5,610,517 | A | 3/1997 | Ma et al. |
| 5,793,206 | A | 8/1998 | Goldfine et al. |
| RE36,986 | E | 12/2000 | Melcher |
| 6,188,218 | B1 | 2/2001 | Goldfine et al. |
| 6,380,747 | B1 | 4/2002 | Goldfine et al. |
| 2002/0163333 | A1 | 11/2002 | Schlicker et al. |

FOREIGN PATENT DOCUMENTS

EP 1037043 A2 9/2000

OTHER PUBLICATIONS

DOE Phase II Proposal, titled "Intelligent Probes for Ehanced Non-Destructive Determination of Degradation in Hot-Gas-Path Components," Topic #44c, dated Mar. 23, 2002.

(Continued)

*Primary Examiner*—Bot LeDynh
(74) *Attorney, Agent, or Firm*—Hamilton, Brook, Smith & Reynolds, P.C.

(57) ABSTRACT

A process control method is described which uses measurements from magnetic field sensors to monitor the condition of material, such as from a heat treatment process. The sensors can be single element sensors or sensor arrays, can be used to periodically inspect selected locations, mounted to the test material, or scanned over the test material to generate two-dimensional images of the material properties. The sensors can be exposed to the same process conditions as the material, such as elevated temperatures, or the shielding layers can be placed between the test material and the sensors to reduce sensor exposure to the processing conditions. Additional property measurements, such as sensor lift-off, can be used to ensure proper sensors operation.

37 Claims, 13 Drawing Sheets

OTHER PUBLICATIONS

NASA Phase II Proposal, titled "Shaped Field Giant Magnetoresisitive Sensor Arrays for Materials Testing," Topic #01-II A1.05-8767, dated May 2, 2002.

Final Report submitted to NASA, titled "Shaped Field Giant Magnetoresisitive Sensor Arrays for Materials Testing," dated May 3, 2002.

Technical paper titled "Friction Stir Weld Inspection through Conductivity Imaging using Shaped Field MWM—Arrays," Proceedings of the 6th International Conference on Trends in Welding, Callaway Gardens, GA; ASM International, Jan. 2003.

Technical paper titled "Remote Temperature and Stress Monitoring Using Low Frequency Inductive Sensing," SPIE NDE/Health Monitoring of Aerospace Materials and Composites, San Diego, CA, Mar. 2-6, 2003.

Technical paper titled "High Temperature Eddy-Current Sensors for Heat Treatment Monitoring," presented at AeroMat, Jun. 2002.

PROCESS CONTROL AND DAMAGE MONITORING

RELATED APPLICATION

This application claims the benefit of U.S. Provisional Application No. 60/441,691, filed Jan. 21, 2003. The entire teachings of the above application are incorporated herein by reference.

BACKGROUND OF THE INVENTION

The technical field of this invention is that of nondestructive materials characterization, in particular, quantitative, model-based characterization of surface, near-surface, and bulk material condition for flat and curved parts or components using magnetic field based or eddy current sensors.

Characterization of bulk material condition includes measurement of changes in material state caused by fatigue damage, plastic deformation assessment, as well as assessment of residual stress, applied loads, and processing conditions such as, for example, heat treatment, shot peening, roll burnishing, thermal-spray coating, welding or heat treatment. It also may include measurements characterizing the material, such as alloy type, and material states, such as porosity and temperature.

Characterization of surface and near-surface conditions may include measurements of surface roughness, displacement or changes in relative position, coating thickness, and coating conditions. Each of these may involve detection of electromagnetic property changes associated with either microstructural and/or compositional changes, electronic structure (e.g., Fermi surface) or magnetic structure (e.g., domain orientation) changes, or, with single or multiple cracks, cracks or stress variations in magnitude, orientation, or distribution.

Conventional magnetometry, specifically, using eddy current sensors, involves excitation of a conducting winding, the primary, with an electric current source of prescribed frequency. This excitation produces a time-varying magnetic field at the same frequency, which, in turn, may be detected with a sensing winding, the secondary. The spatial distribution of the magnetic field and the field measured by the secondary is influenced by the proximity and physical properties (electrical conductivity and magnetic permeability) of nearby materials. When the sensor is intentionally placed in close proximity to a test material, the physical properties of the material can be deduced from measurements of the self-impedance of the primary winding or the impedance between the primary and secondary windings. Traditionally, scanning of eddy current sensor across the material surface has been used to detect flaws.

For process and damage monitoring, including at elevated temperatures, it is desirable to detect and monitor material property changes during processing or to detect and monitor material damage during high-temperature service, as early as possible. This early detection allows process control and optimization in the case of process monitoring, and provides an early warning of potentially unsafe conditions in the case of the material damage monitoring. This is particularly critical for control of heat treatment processes such as steel tempering, alloy aging/precipitation hardening or other high-temperature processes as well as in-service monitoring of components operating at high temperatures.

As an example, steel tempering is typically done at temperatures between 350 and 1200° F., with lower temperatures producing higher strength steels. Aging is performed for a wide range of materials, including precipitation-hardening steels, nickel alloys, titanium alloys, aluminum alloys, magnesium alloys, etc. Aging temperature range depends on the class of materials. Some typical temperature ranges are: 900 to 1150° F. for precipitation-hardening steels, 800 to 1200° F. for titanium alloys, 250 to 675° F. for aluminum alloys, and 250 to 450° F. for magnesium alloys.

One limitation for the use of conventional eddy current sensors in high temperature applications are the calibrations requirements for meaningful property measurements. The calibration typically involves adjustment of the amplitude and phase (or the in-phase and out-of-phase) components to preselected conditions when the sensor is placed in well-defined proximity to the reference standard material having known properties. Since typical coils have many winding turns and the response is generally temperature sensitive, the reference standard needs to be at the same temperature as the test material and, for that matter, the sensor and associated instrumentation should also be at the nominal operating temperature under which the measurements will be performed. Otherwise, the elevated temperature measurements may be incorrect.

SUMMARY OF THE INVENTION

This application focuses specifically on monitoring material property changes for process control, as well as for detection of material damage, particularly at elevated temperatures. Aspects of the methods described herein involve novel sensors and sensor arrays for the measurement of the near surface properties of conducting and/or magnetic materials. These sensors and arrays use novel geometries for the primary winding and sensing elements that promote accurate modeling of the response and provide enhanced observability of property changes of the test material.

In one embodiment of the invention, there are methods for monitoring of material properties as they are changed during processing, inferring the material condition from these properties, and using these results to control the process. This may involve disposing an electromagnetic sensor, such as an electric field based capacitive sensor or magnetic field based sensor such as an eddy current sensor or sensor array, in proximity to the test material and converting the response of each sensor or each sense element into a measurement of an effective material property.

In one embodiment of the invention, the electrical property may be the magnetic permeability and in another the electrical property may be the electrical conductivity.

In one embodiment of the invention, the sense elements may be sensing coils that respond to absolute changes in the magnetic field response. In another embodiment of the invention, the sense elements incorporate giant magnetoresistive sensors.

The sensor may be mounted against the surface or scanned over the surface of the material. Preferably, the sensor is not in contact with the surface of the test material to help minimize any effects the monitoring system may have on the environment around the material being processed.

As part of the process control, the measured properties which reflect the condition of the material may be compared to those predicted for the material condition. This comparison may be a simple difference, including a scale factor, which may then be used for feedback in the process control. In one embodiment of the invention, the process being monitored may be the heat treatment of the material. Preferably, another sensor, such as a thermocouple, is then used to monitor the temperature of the materials. This measured temperature may then be used in the estimate of the material condition so that any divergence of measured and estimated properties can be used to bring the process back under control.

In one embodiment of the invention, the sensor is exposed to the same processing conditions as the test material, such as an oven or a furnace for a heat treatment process. Alternatively, the sensor may be exposed to different conditions than the material, but the measured properties still must reflect the material condition. Exposure to different conditions or shielding from the processing conditions may be accomplished by inserting a layer between the sensor and test materials, such as the wall of an oven or furnace.

In yet another embodiment of the invention, additional property information obtained from the sensors may be used to ensure proper sensor operation. In a preferred embodiment of the invention, the lift-off of each sensing element is used to ensure that it is within an expected range.

In another embodiment of the invention, a sensor is calibrated in-situ by placing the sensor near the test material, exposing the material to a process condition, and adjusting the sensor response based on a known relationship between the process condition and the material properties. Preferably, this is performed with eddy current sensors and eddy current sensor arrays. In one embodiment of the invention, the material property is an electrical conductivity. Also, in one embodiment of the invention, the process is a heat treatment so that the process condition is a temperature.

In another embodiment of the invention, for process control, the relationship between an electrical property and a process condition is determined from values obtained from a sensor that measures absolute electrical properties and known process conditions. Preferably, this is performed with eddy current sensors and eddy current sensor arrays. In one embodiment of the invention, the material property is an electrical conductivity. Also, in one embodiment of the invention, the process is a heat treatment so that the process condition is a temperature.

In a preferred embodiment of the invention, when the electrical property is the electrical conductivity and the process condition is temperature, the relationship is linear. This relationship can be determined during the initial heating transient for the process. Once determined, the relationship can then be used for subsequent process control so that any divergence between the measured electrical properties and those obtained from the relationship to the process condition can be input as feedback into a process controller.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
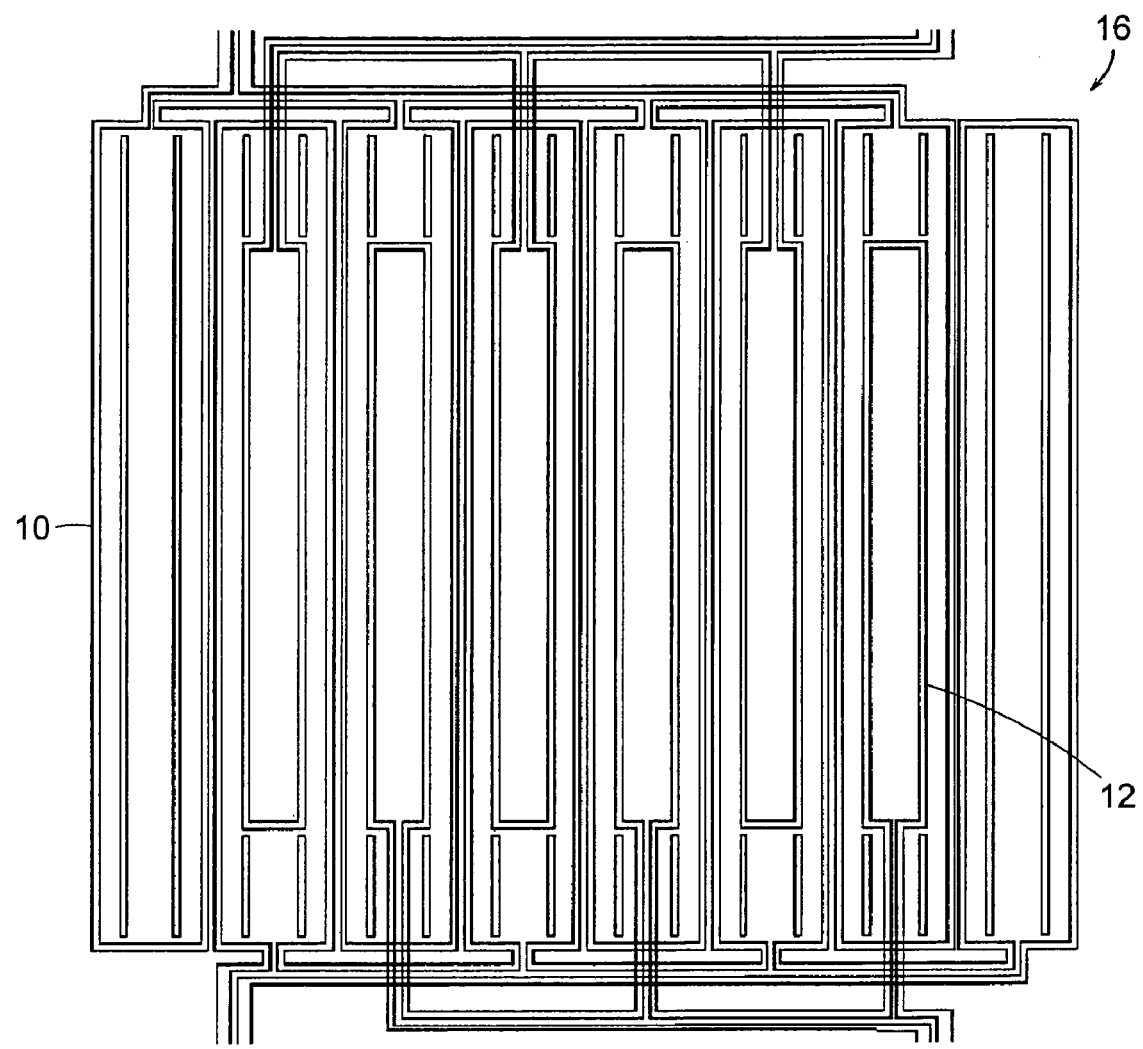
FIG. 1 is a schematic drawing of a spatially periodic field eddy-current sensor.

A description of preferred embodiments of the invention follows.

The use of conformable and nonconformable eddy-current sensors and sensor arrays is described herein for the nondestructive characterization of materials, particularly as it applies to the elevated temperature monitoring of processes and/or damage. This characterization includes surface mounted and scanning, contact and noncontact configurations. This sensing approach can be used to monitor material characteristics at a given location with single or multiple sensing element sensors, sensor arrays and/or networks of surface mounted sensors using hand-held probes, mounted into automated scanners or as part of an embedded network.

The sensors can be mounted into a structure in proximity to a material under test for monitoring the property changes while the material is being stressed and fatigued. Alternatively, such embedded sensors can be queried with instrumentation on a scheduled or unscheduled basis with either no electronics on board or minimal electronics on board, and by plugging in at an easy access location. The sensors can also be used to detect process related changes in the material properties, such as grinding burns in steels either as a part of in-process monitoring or at any time after processing, i.e., during quality control inspections or in service.

A conformable eddy-current sensor suitable for these measurements, the Meandering Winding Magnetometer (MWM®), is described in U.S. Pat. Nos. 5,015,951, 5,453, 689, and 5,793,206, all of which are incorporated by reference in their entirety herein. The MWM is a "planar," conformable eddy-current sensor that was designed to support quantitative and autonomous data interpretation methods. These methods, called grid measurement methods, permit crack detection on curved surfaces without the use of crack standards, and provide quantitative images of absolute electrical properties (conductivity and permeability) and coating thickness without requiring field reference standards (i.e., calibration can be performed in "air," away from conducting surfaces). MWM sensors and MWM-Arrays can be used for characterization of materials and process-induced surface layers. Characteristics of these sensors and sensor arrays include directional multi-frequency magnetic permeability or electrical conductivity measurements over a wide range of frequencies, e.g., from 250 Hz to 40 MHz with the same MWM sensor or MWM-Array, high-resolution imaging of measured permeability or conductivity, rapid permeability or conductivity measurements with or without a contact with the surface, and a measurement capability on complex surfaces with a hand-held probe or with an automated scanner. Significantly, the MWM was designed to be insensitive to variations in its own temperature, which makes it well-suited to non-isothermal processing conditions. In contrast, conventional eddy current sensors often require extensive calibration standards and reference parts that mimic both the geometry and conditions (e.g., temperatures) of the test article. Note that changing the excitation frequency also changes the depth of penetration of the magnetic field into the test material so that multiple frequency measurements can be used to infer material property variations with depth into the material.

These sensors can be placed or mounted on conducting or magnetic materials, for example, metals, and used to monitor property changes during processing or while in service. Output from MWM monitoring property changes during processing can be used for process control and output from MWM in-service monitoring can provide assessment of material damage, including deleterious microstructural changes as well as crack initiation and growth. For high temperature applications, the MWM can be fabricated onto a variety of electrically insulating substrates, such as ceramics. The substrate and electrically insulating overcoats on top of the sensor also provide mechanical robustness, which is critical for contact applications where a high pressure may be present to hold the sensor against the test article.

The MWM can be fabricated as single sensing elements for local property measurements and as distributed arrays (MWM-Arrays) for rapid measurements over larger areas. A single array of elements can be used to monitor process changes, such as in a welding operation. With multiple sensing elements distributed across a process affected zone, images of the absolute properties can be obtained by scanning the array across the process affected zone or with a stationary sensor if the tool tip moves across the sensor array. Any sensing elements located beyond the process affected zone can be used to determine base or reference material properties. This array of elements can be used to provide real-time feedback to the process controllers and aide in positioning of the processing tool.

In some processing applications, the MWM sensors or MWM-Arrays must not modify the environment around the material being tested. For example, if a sensor is placed in contact with the test article, the local temperature will be slightly different than the temperature of nearby, uncovered material. In these situations, the sensors can be configured for non-contact measurements where an air-gap is intentionally created between the sensor and the test article. Again, the MWM and MWM-Arrays are well-suited to this type of measurement as the sensor and Grid measurement methods can provide independent measures of the proximity (air-gap thickness) and material properties. This is particularly critical for applications where the air-gap thickness may not be constant each time the sensor is placed near the test article.

FIG. 1 illustrates the basic geometry of an the MWM sensor 16, a detailed description of which is given in U.S. Pat. Nos. 5,453,689, 5,793,206, and 6,188,218 and U.S. patent application Ser. Nos. 09/666,879 and 09/666,524, both filed on Sep. 20, 2000, the entire teachings of which are incorporated herein by reference. The sensor includes a primary winding 10 having extended portions for creating the magnetic field and secondary windings 12 within the primary winding for sensing the response. The primary winding is fabricated in a spatially periodic pattern with the dimension of the spatial periodicity termed the spatial wavelength $\lambda$. A current is applied to the primary winding to create a magnetic field and the response of the material under test (MUT) to the magnetic field is determined through the voltage measured at the terminals of the secondary windings. This geometry creates a magnetic field distribution similar to that of a single meandering winding. A single element sensor has all of the sensing elements connected together. The magnetic vector potential produced by the current in the primary can be accurately modeled as a Fourier series summation of spatial sinusoids, with the dominant mode having the spatial wavelength $\lambda$. For an MWM-Array, responses from individual or combinations of the secondary windings can be used to provide a plurality of sense signals for a single primary winding construct as described in U.S. Pat. No. 5,793,206 and RE36,986.

Figure 2:
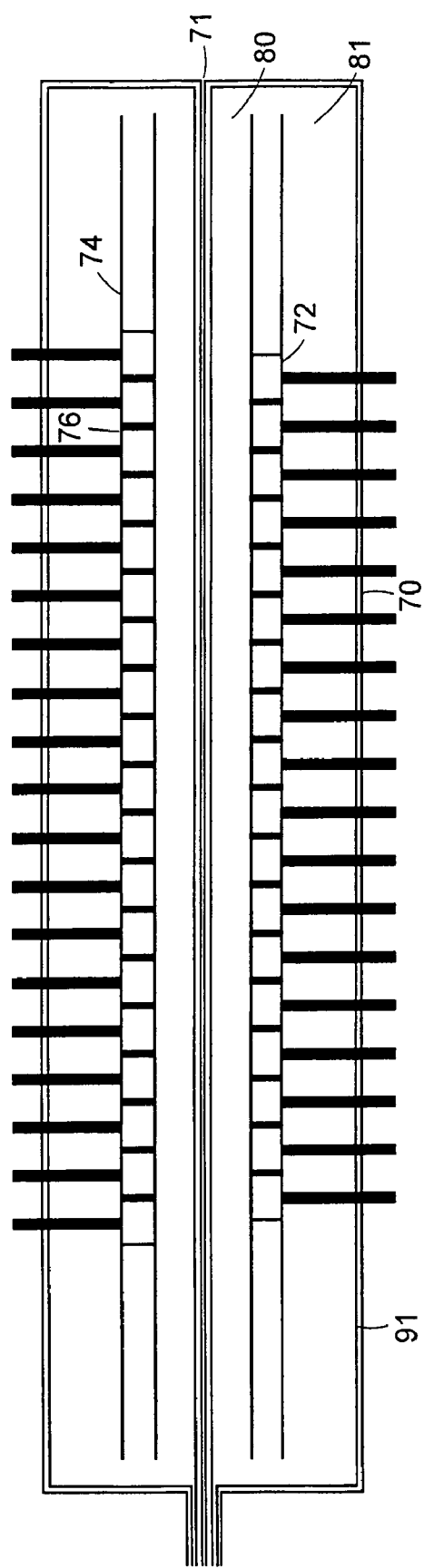
FIG. 2 is an expanded view of the drive and sense elements for an eddy-current array having offset rows of sensing elements.
Figure 3:
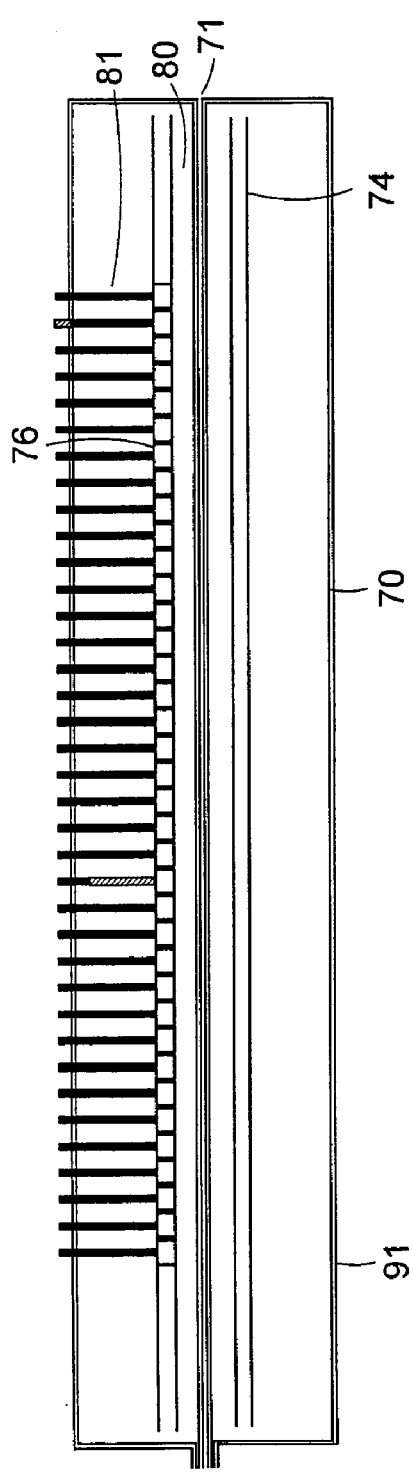
FIG. 3 is an expanded view of the drive and sense elements for an eddy-current array having a single row of sensing elements.
Figure 4:
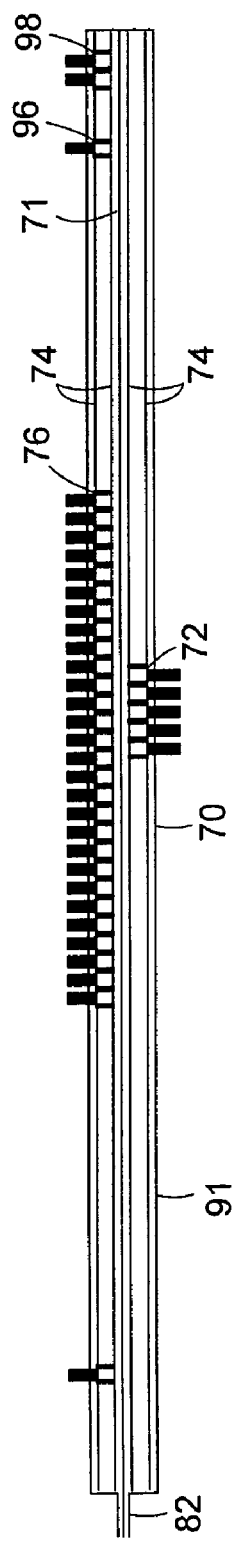
FIG. 4 is an expanded view of an eddy-current array where the locations of the sensing elements along the array are staggered.

Eddy-current sensor arrays comprised of one or more drive windings, (possibly a single rectangle) and multiple sensing elements can be used to inspect the test material. Example sensor arrays are shown in FIG. 2 through FIG. 4 some embodiments of which are described in detail in U.S. patent application Ser. No. 10/102,620, filed Mar. 19, 2002, and Ser. No. 10/010,062, filed Mar. 13, 2001, the entire teachings of which are incorporated herein by reference. These arrays include a primary winding 70 having extended portions for creating the magnetic field and a plurality of secondary elements 76 within the primary winding for sensing the response to the MUT. The secondary elements are pulled back from the connecting portions of the primary winding to minimize end effect coupling of the magnetic field. Dummy elements 74 can be placed between the meanders of the primary to maintain the symmetry of the magnetic field, as described in U.S. Pat. No. 6,188,218. When the sensor is scanned across a part or when a crack propagates across the sensor, perpendicular to the extended portions of the primary winding, secondary elements 72 in a primary winding loop adjacent to the first array of sense elements 76 provide a complementary measurement of the part properties. These arrays of secondary elements 72 can be aligned with the first array of elements 76 so that images of the material properties will be duplicated by the second array (improving signal-to-noise through combining the responses or providing sensitivity on opposite sides of a feature such as a fastener, as described in U.S. patent application Ser. Nos. 10/102,620 and 10/010,062. Alternatively, to provide complete coverage when the sensor is scanned across a part the sensing elements, it can be offset along the length of the primary loop or when a crack propagates across the sensor, perpendicular to the extended portions of the primary winding, as illustrated in FIG. 2.

The sensor and sensor array can be reconfigured with the geometry of the drive and sense elements and the placement of the sensing elements adjusted to improve sensitivity for a specific inspection. For example, the MWM is most sensitive to cracks when the cracks are oriented perpendicular to the drive windings and located under or near the drive windings. Thus the winding pattern can be designed or selected to accommodate anticipated crack distributions and orientations. In cases where cracks oriented in all directions must be detected, stacked MWM-Arrays with orthogonal drive windings can be used. An example of a modified design is shown in FIG. 4. Here, most of the sensing elements 76 are located in a single row to provide the basic image of the material properties. A small number of sensing elements 72 are offset from this row to create a higher image resolution in a specific location. Other sensing elements are distant from the main grouping of sensing elements at the center of the drive windings to measure relatively distant material properties, such as the base material properties for plates at a lap joint or a weld.

Figure 5:
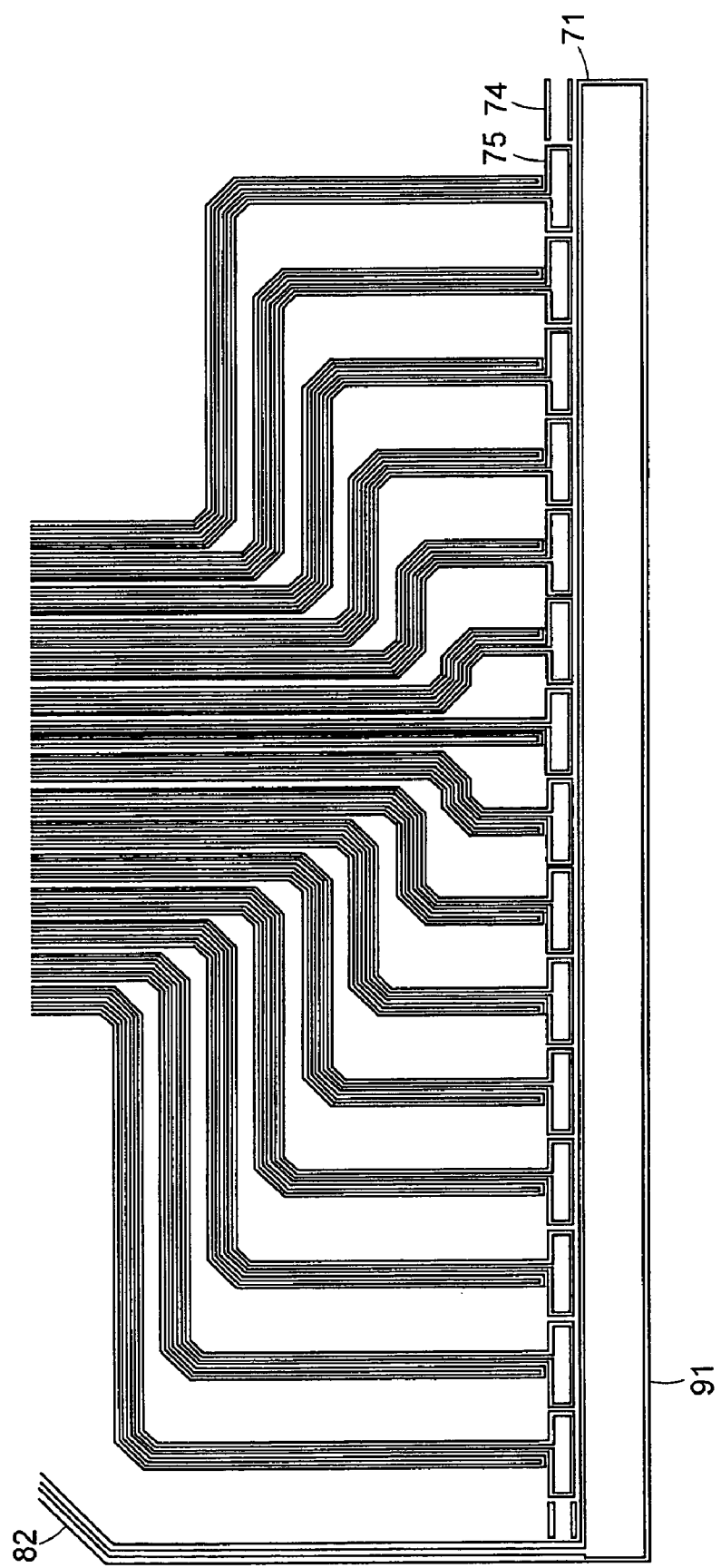
FIG. 5 is an expanded view of an eddy current array with a single rectangular loop drive winding and a linear row of sense elements on the outside of the extended portion of the loop.

In one embodiment of the invention, the number of conductors used in the primary winding can be reduced further so that a single rectangular drive is used. As shown in FIG. 5, a single loop having extended portions is used for the primary winding. A row of sensing elements 75 is placed on the outside of one of the extended portions. This is similar to designs described in U.S. Pat. No. 5,453,689 where the effective wavelength of the dominant spatial field mode is related to the spacing between the drive winding and sensing elements. This spacing can be varied to change the depth of sensitivity to properties and defects. The sensing elements can be placed in different layers to provide multiple lift-offs at the same or different positions.

The MWM sensor and sensor array structure can be produced using micro-fabrication techniques typically employed in integrated circuit and flexible circuit manufacture. This results in highly reliable and highly repeatable sensors, which results in nearly identical magnetic field distributions around the windings. In contrast, the coils used in conventional eddy current sensors are not reproducible, which introduces severe requirements for calibration of the sensors (e.g., matched sensor/calibration block sets). As the sensor was also designed to produce a spatially periodic magnetic field in the MUT, the sensor response can be accurately modeled which dramatically reduces calibration requirements. For example, calibration in air can be used to measure an absolute electrical conductivity without calibration standards, which makes the sensor geometry well-suited to surface mounted or embedded applications where calibration requirements are necessarily relaxed.

For applications at temperatures up to 120° C. (250° F.), the windings are typically mounted on a thin and flexible substrate, producing a conformable sensor. A higher temperature version has shown a good performance up to about 270° C. (520° F.). In another embodiment of the invention these sensors can be fabricated onto ceramic substrates or with platinum leads and Boron Nitride coatings or other means to extend their operating temperature range. Bond pads can be placed on the back sides of the sensor or array, with vias used for electrical continuity through the substrate material, so that sensor face can remain essentially flat. Electrical connections to the sensor are made through these bond pads. For contact measurements, a second layer of ceramic may be placed over the surface of the sensor (i.e., an overcoat between the sensor and the MUT) to prevent shorting of the windings by the MUT. For conformable sensors, the insulating layers can be a flexible material such as Kapton™, a polyimide available from E. I. DuPont de Nemours Company, while for high temperature applications the insulating layers can be a ceramic such as alumina. Although not generally flexible, these ceramic substrate arrays can be molded into the shape of the test article.

For measuring the response of the individual sensing elements in an array, multiplexing between the elements can be performed. However, this may significantly reduce the data acquisition rate, so a preferable approach is to use an impedance measurement architecture that effectively allows the acquisition of data from all of the sense elements in parallel. Furthermore, the ability to measure the MUT properties at multiple frequencies extends the capability of the inspection to better characterize the material and/or geometric properties under investigation. This type of instrument is described in detail in U.S. patent application Ser. No. 10/155,887, filed May 23, 2002, the entire teachings of which are incorporated herein by reference. The use of multiple sensing elements with one meandering drive and parallel architecture measurement instrumentation then permits high image resolution in real-time and sensitivity with relatively deep penetration of fields into MUT.

An efficient method for converting the response of the MWM sensor into material or geometric properties is to use grid measurement methods. These methods map the magnitude and phase of the sensor impedance into the properties to be determined and provide for a real-time measurement capability. The measurement grids are two-dimensional databases that can be visualized as "grids" that relate two measured parameters to two unknowns, such as the magnetic permeability (or electrical conductivity) and lift-off (where lift-off is defined as the proximity of the MUT to the plane of the MWM windings). For the characterization of coatings or surface layer properties, three- (or more)-dimensional versions of the measurement grids, called lattices and hypercubes, respectively, can be used. Alternatively, the surface layer parameters can be determined from numerical algorithms that minimize the least-squares error between the measurements and the predicted responses from the sensor, or by intelligent interpolation search methods within the grids, lattices or hypercubes.

An advantage of the measurement grid method is that it allows for real-time measurements of the absolute electrical properties of the material and geometric parameters of interest. The database of the sensor responses can be generated prior to the data acquisition on the part itself, so that only table lookup and interpolation operations, which are relatively fast, have to be performed. Furthermore, grids can be generated for the individual elements in an array, so that each individual element can be lift-off compensated to provide absolute property measurements, such as the electrical conductivity. This again reduces the need for extensive calibration standards. In contrast, conventional eddy-current methods that use empirical correlation tables that relate the amplitude and phase of a lift-off compensated signal to parameters or properties of interest, such as crack size or hardness, require extensive calibrations using standards and instrument preparation.

Figure 6:
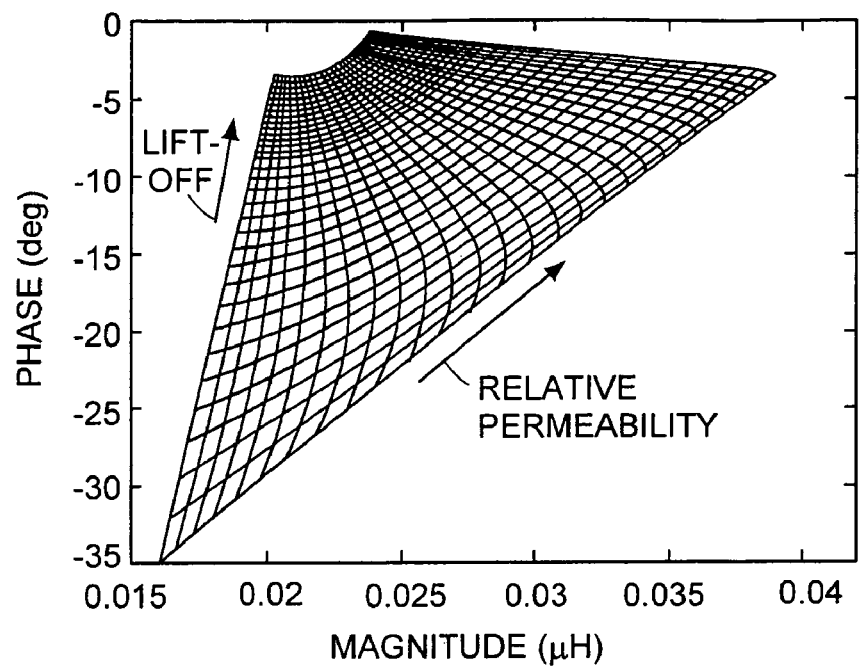
FIG. 6 illustrates a representative measurement grid relating the magnitude and phase of the sensor terminal impedance to the lift-off and magnetic permeability.
Figure 7:
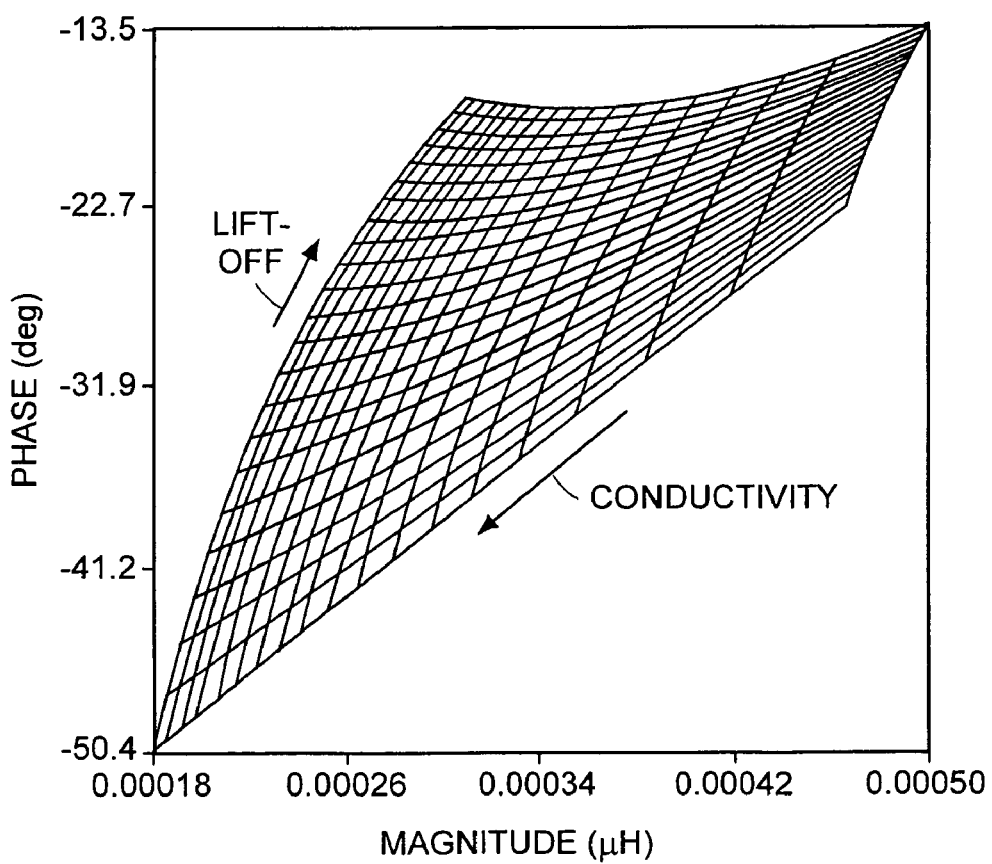
FIG. 7 illustrates a representative measurement grid relating the magnitude and phase of the sensor terminal impedance to the lift-off and electrical conductivity.

For ferromagnetic materials, such as most steels, a measurement grid provides conversion of raw data to magnetic permeability and lift-off. A representative measurement grid for ferromagnetic materials (e.g., carbon and alloy steels) is illustrated in FIG. 6. A representative measurement grid for a low-conductivity nonmagnetic alloy (e.g., titanium alloys, some superalloys, and austenitic stainless steels) is illustrated in FIG. 7. For coated materials, such as cadmium and cadmium alloys on steels, the properties of the coatings can be incorporated into the model response for the sensor so that the measurement grid accurately reflects, for example, the permeability variations of substrate material with stress and the lift-off. Lattices and hypercubes can be used to include variations in coating properties (thickness, conductivity, permeability), over the imaging region of interest.

Figure 8A:
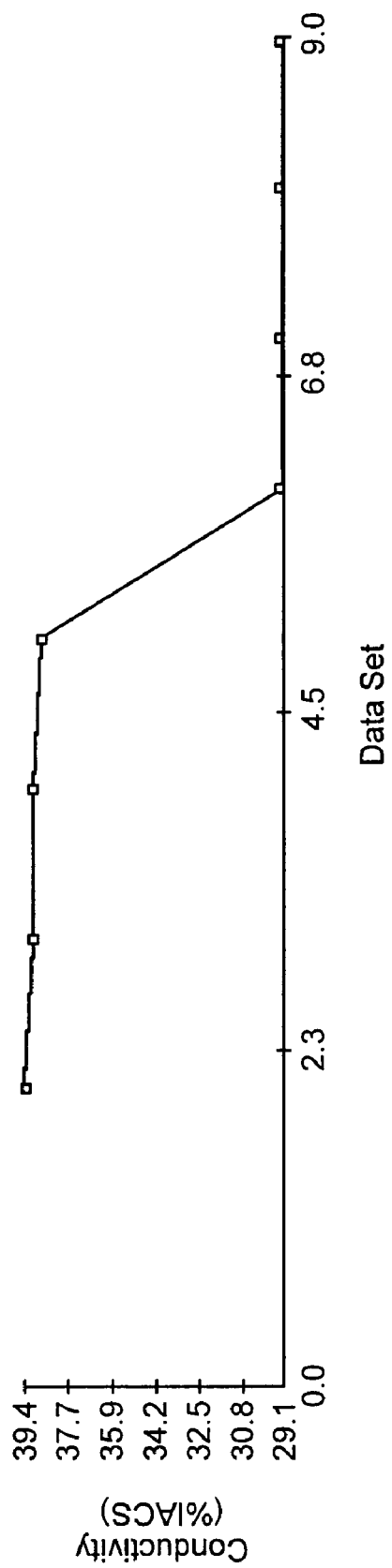
FIG. 8A illustrates several electrical conductivity measurements with an MWM-Array for two aluminum alloys at room temperature.
Figure 8B:
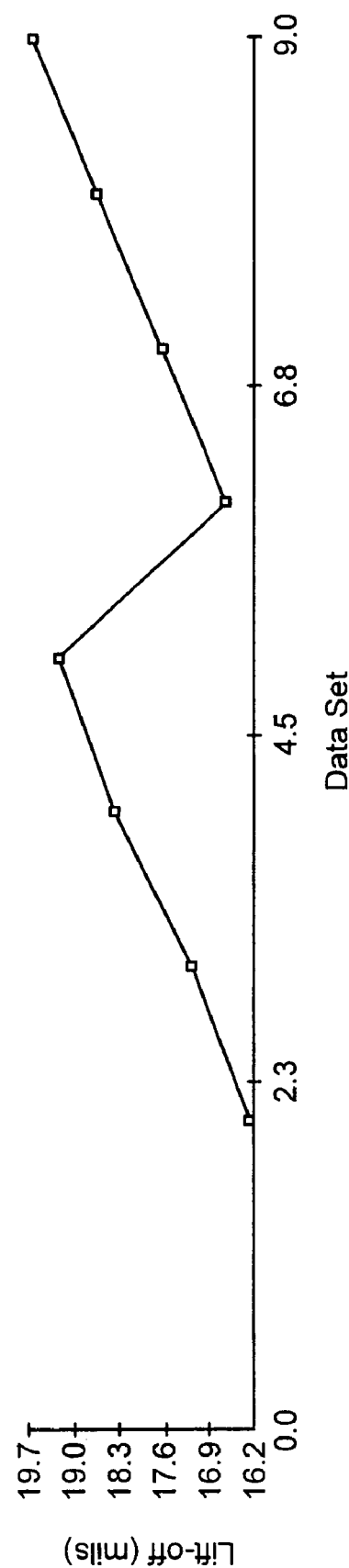
FIG. 8B illustrates lift-off measurements corresponding to the measurements of FIG. 8A.

FIG. 8 shows a representative set of room temperature data taken with an MWM-Array fabricated onto a ceramic substrate on two alloys of aluminum. FIG. 8A shows the measured electrical conductivity values while FIG. 8B shows the measured lift-offs. In this case, the lift-off was intentionally varied by placing insulating shims between the MWM-Array and the test material. FIG. 8 illustrates that the measured conductivity is essentially constant for each alloy (7050 and 2024SP) as the lift-off is varies and demonstrates the independence of the conductivity and lift-off measurements.

Figure 9A:
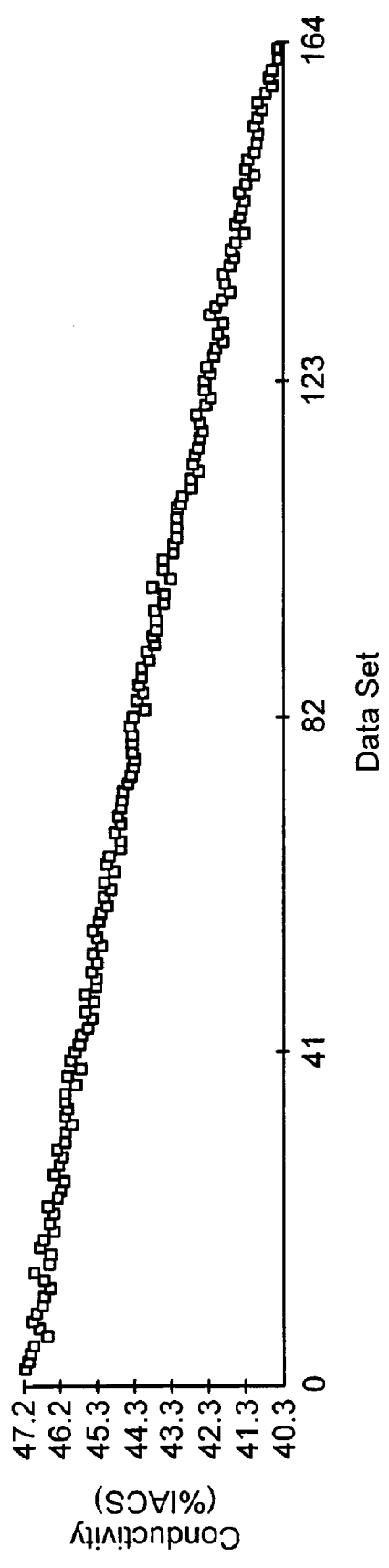
FIG. 9A illustrates electrical conductivity variation as the temperature (or data set number) increases for an aluminum alloy.
Figure 9B:
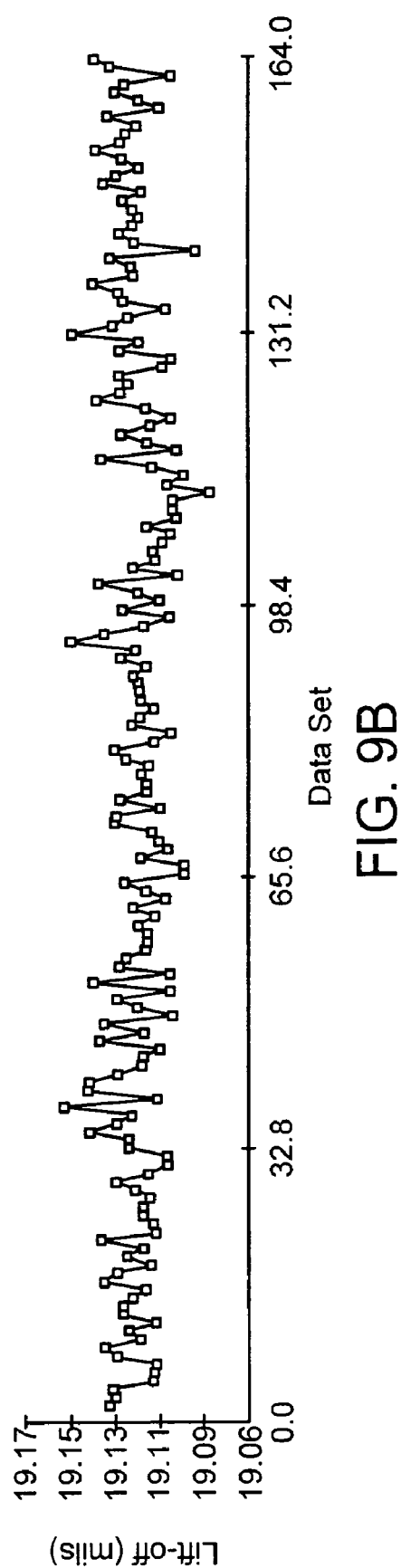
FIG. 9B illustrates lift-off measurements corresponding to the measurements of FIG. 9A.

FIG. 9 shows another set of data taken with an MWM-Array on an aluminum alloy as the temperature is varied. In this case, the aluminum test article was placed on a hot plate and the MWM-Array was supported above the aluminum using insulating shims. FIG. 9A shows the measured electrical conductivity while FIG. 9B shows the measured lift-off. Data was taken periodically so that the data set number increases with time. The conductivity of the aluminum is observed to decrease with increasing temperature (i.e., increasing data set number), as expected, while the lift-off remains essentially constant. This demonstrates the capability of the high temperature array to perform eddy current measurements at elevated temperatures.

The MWM sensors and sensor arrays can also be used to monitor heat treatment of metals and for monitoring high temperature tests on metals and alloys, metal processing and the condition of elevated temperature components. Monitoring of these properties can be done in-situ, with the sensor itself also exposed to elevated temperatures, such as in a furnace, so that processing conditions can be adjusted as necessary to ensure a proper heat treatment. For example, an MWM sensor placed near a material being treated could provide effective electrical conductivity information while the temperature of the material could also be monitored, possibly with a thermocouple. Then, given the temperature, one could calculate the expected conductivity, using relations like the standard linear conductivity inverse dependence on temperature, and compare this expected conductivity with the measured conductivity. Any differences or divergence could be used as an input to a feedback control algorithm to adjust the process. The divergence may indicate damage conditions as well so that the treatment must be stopped. Processes that expose the material to low temperatures could be controlled in a similar fashion.

Figure 10:
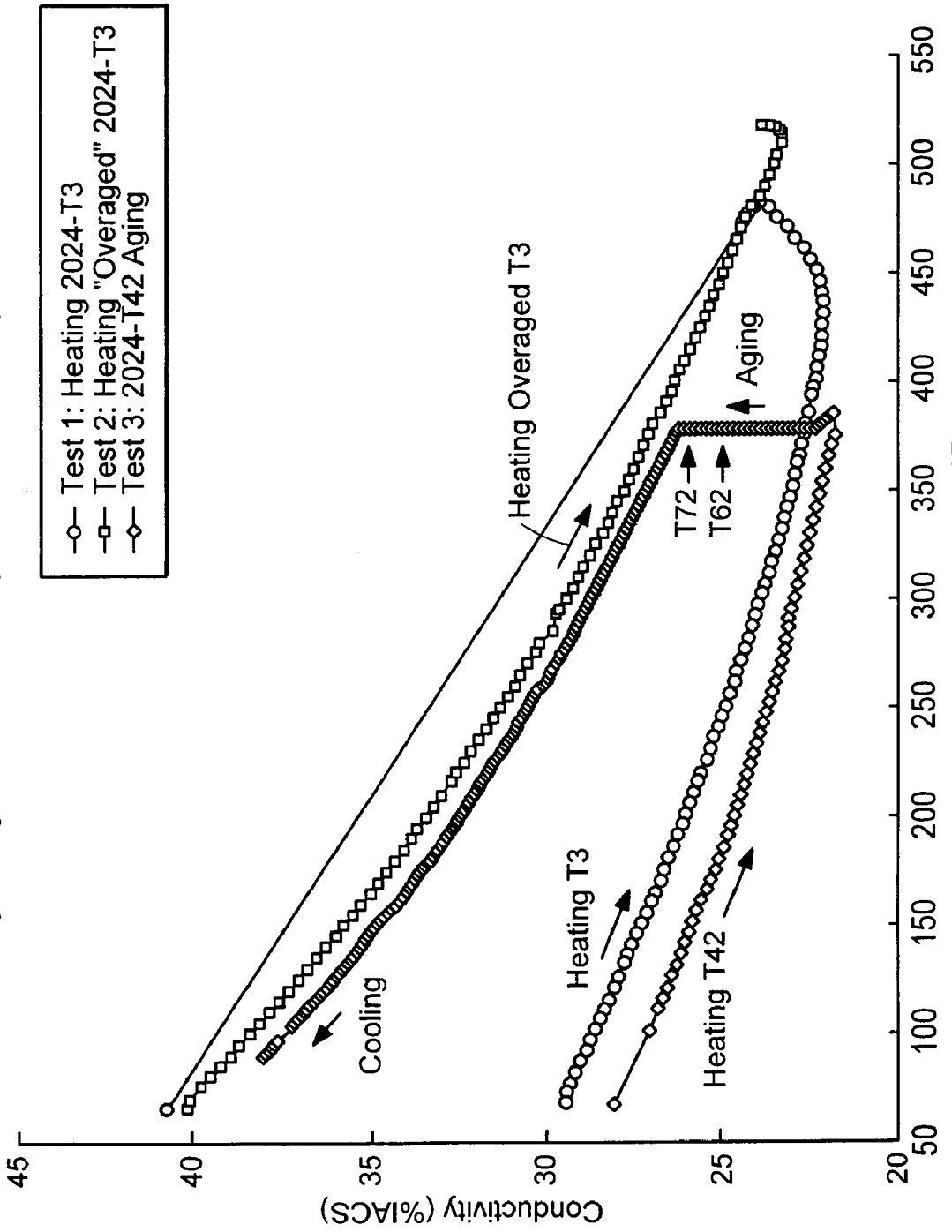
FIG. 10 illustrates MWM measured conductivity changes for Al 2024 at temperatures up to 270° C.
Figure 11:
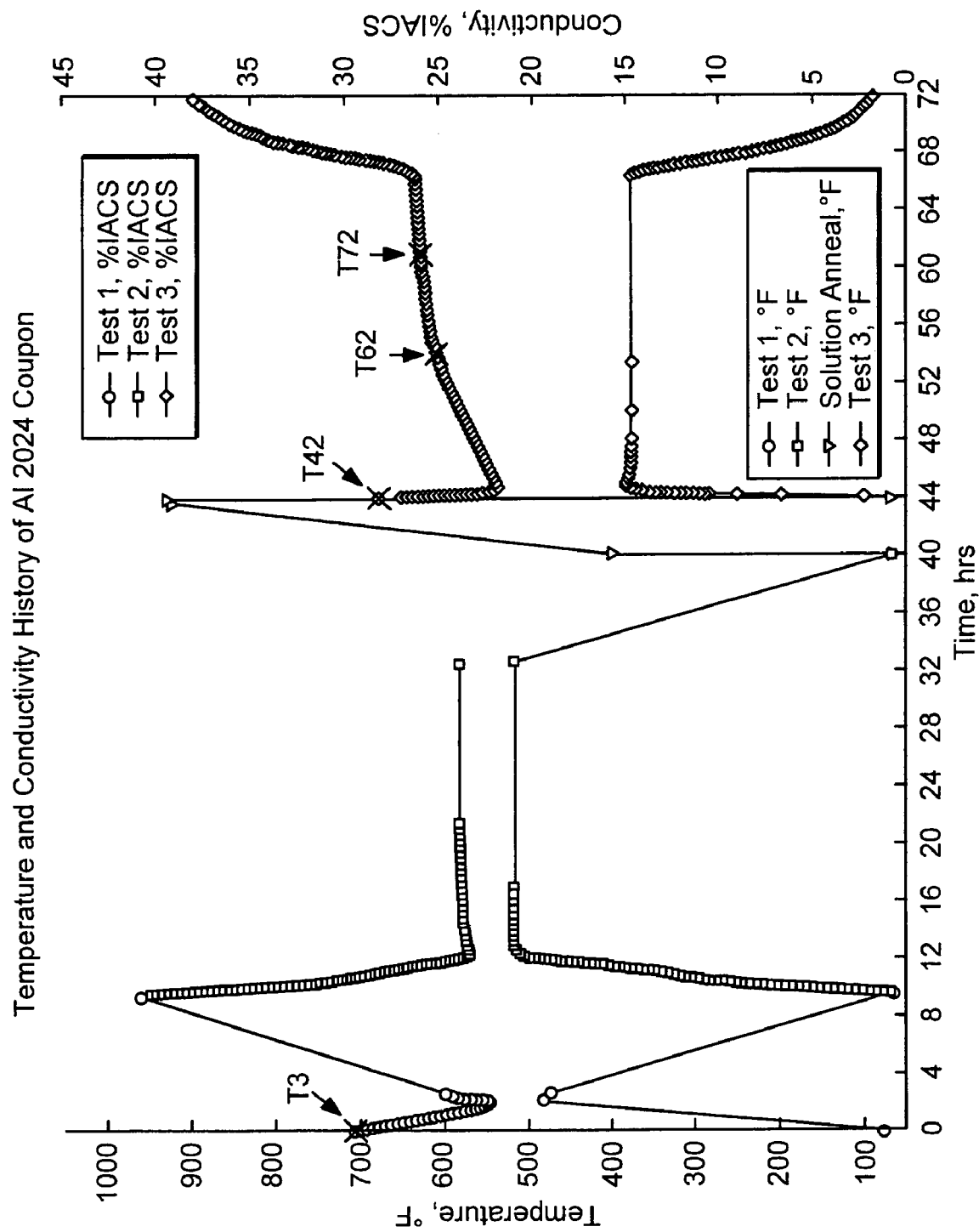
FIG. 11 illustrates the temperature and conductivity history for an Al 2024 coupon heat treatment.
Figure 12:
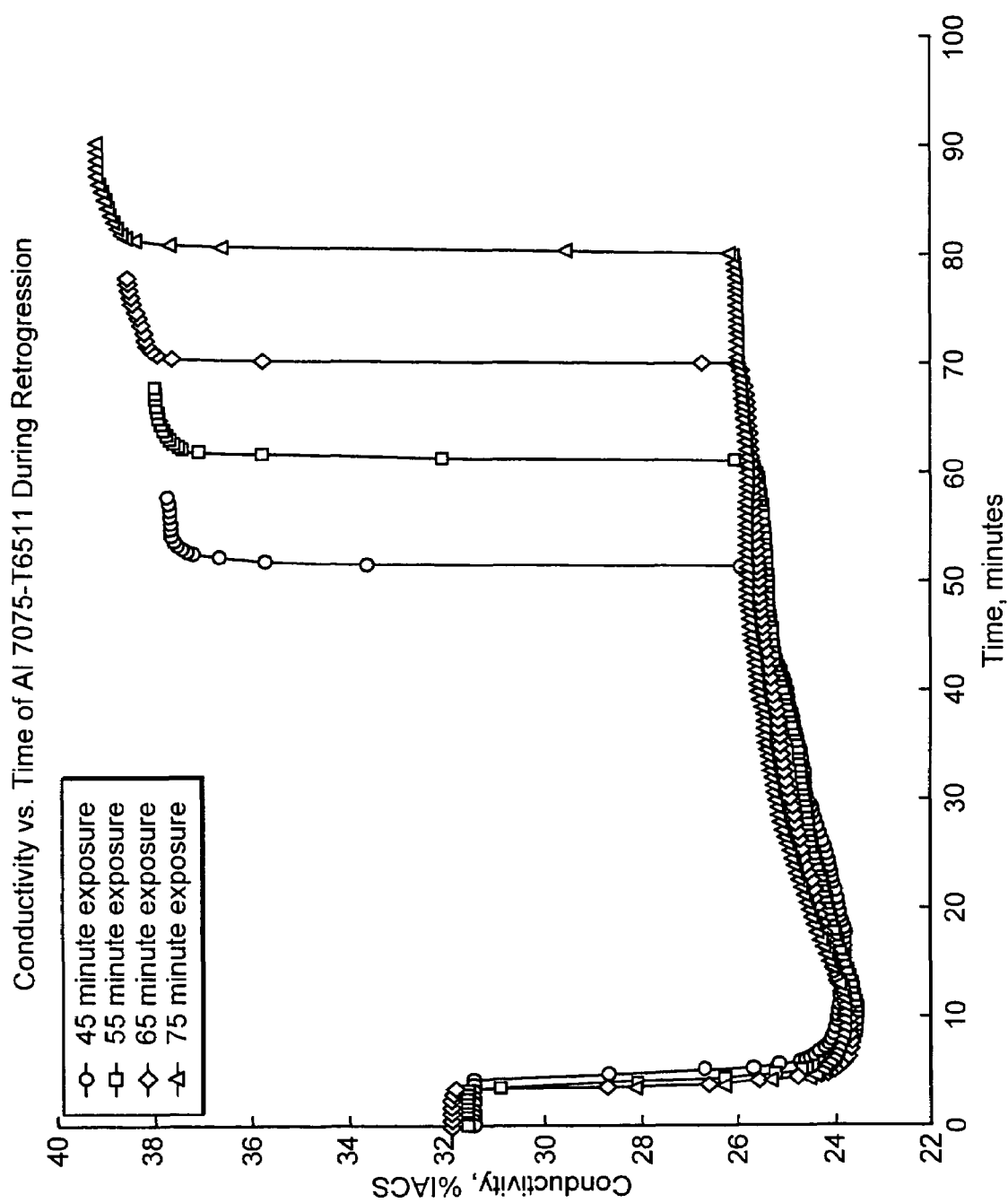
FIG. 12 illustrates MWM measured conductivity transient of Al 7075 during retrogression.

FIG. 10 shows the results of standard MWM configuration lift-off and conductivity measurements of an aluminum 2024 coupon during various heat treatments at temperatures up to 270° C. The plots shows conductivity versus temperature for an aluminum 2024 coupon as the original T3 condition was overaged and then reheated. Following a solution anneal to produce the T42 condition, the coupon was again heated to monitor conductivity changes as the T62, T72 and overaged conditions were achieved. These measurements used a single-channel MWM sensor constructed of copper conductors on a Kapton™ substrate placed inside an oven along with the treated material. The associated impedance measurement instrumentation was kept outside the oven, with cables connecting the sensor to the instrument. FIG. 11 shows the corresponding temperature and conductivity history, which illustrates the capability of the sensor to monitor the processing of the metal and the condition during the treatment. Similarly, FIG. 12 illustrates the alloy condition changes during retrogression. The conductivity drops dramatically after the coupon is placed in the furnace. Then, after dwelling at or exposing the coupon to an elevated temperature such as 400° F. the coupon is quenched. This results in a higher electrical conductivity than was present initially, with the effect depending on the exposure duration.

The sensor or sensor array being used as part of the process control does not necessarily have to be exposed to the same environment as the treated material if the material condition can be monitored externally. For example, alternative sensing elements such as magnetoresistive, giant magnetoresistive, or flux gate sensors can be used with the MWM primary winding geometry and operated at low excitation frequencies so that the associated magnetic fields penetrate deep into materials or through intermediates between the sensor and the test material. The use of such sensing elements is described in more detail in U.S. patent application Ser. No. 10/045,650 filed on Nov. 8, 2001, and Ser. No. 10/441,976 filed on May 20, 2003, the entire teachings of which are hereby incorporated by reference.

Figure 13:
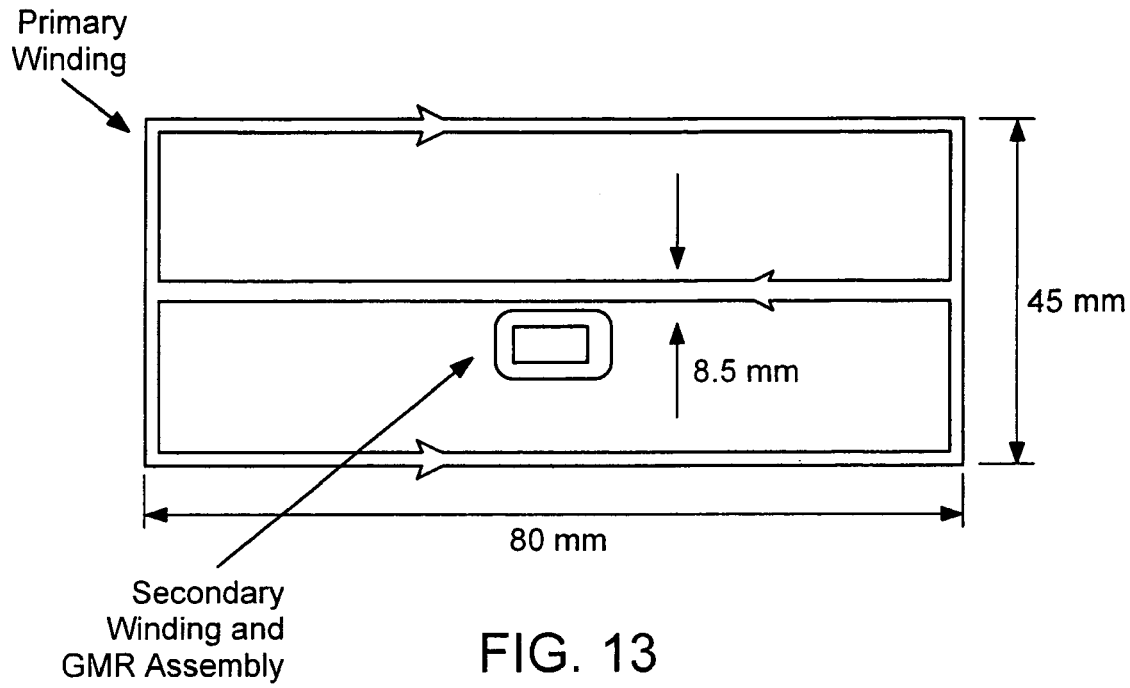
FIG. 13 illustrates a layout for a single turn Cartesian geometry GMR magnetometer.

An example rectangular or Cartesian-geometry GMR-based magnetometer is illustrated in FIG. 13. The parallel primary windings are laid out in a fashion similar to the MWM-Array designs. The winding layout of FIG. 13 allows the relative polarity of the two constituent current loops to be changed to generate a structure with twice the effective wavelength. This permits inspection at two different depths, at a single frequency. For the results presented here, the currents were directed as shown, with the center leg of the winding carrying twice the current of the two edge (or return) windings. The two half-wavelength current loops have identical areas and oppositely directed currents of equal magnitude, so that their effective dipole moments cancel out, resulting in no net dipole moment in the far field. Here the dominant far-field moment is a quadrupole. This elimination of the net dipole moment of the sensor improves measurement reliability because it reduces the sensitivity of the magnetometer to objects outside its nominal range of sensitivity.

Figure 14:
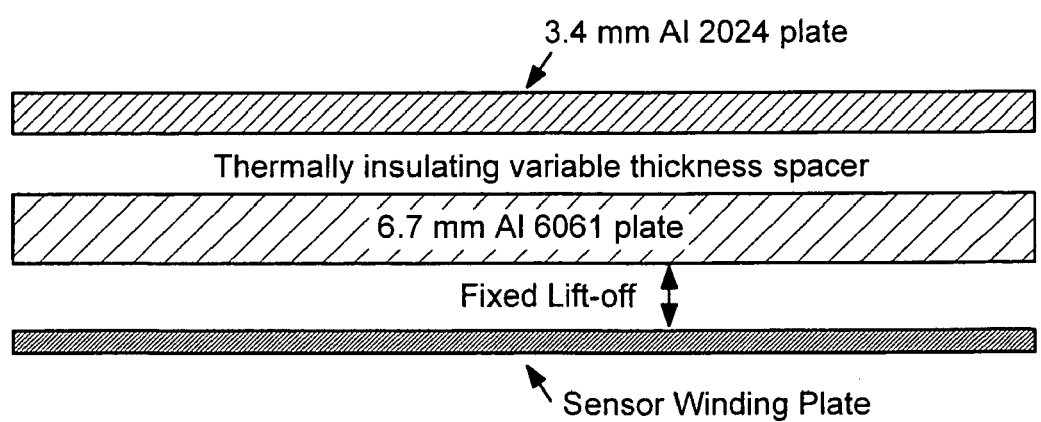
FIG. 14 is a schematic for remotely monitoring the temperature of a plate.
Figure 15:
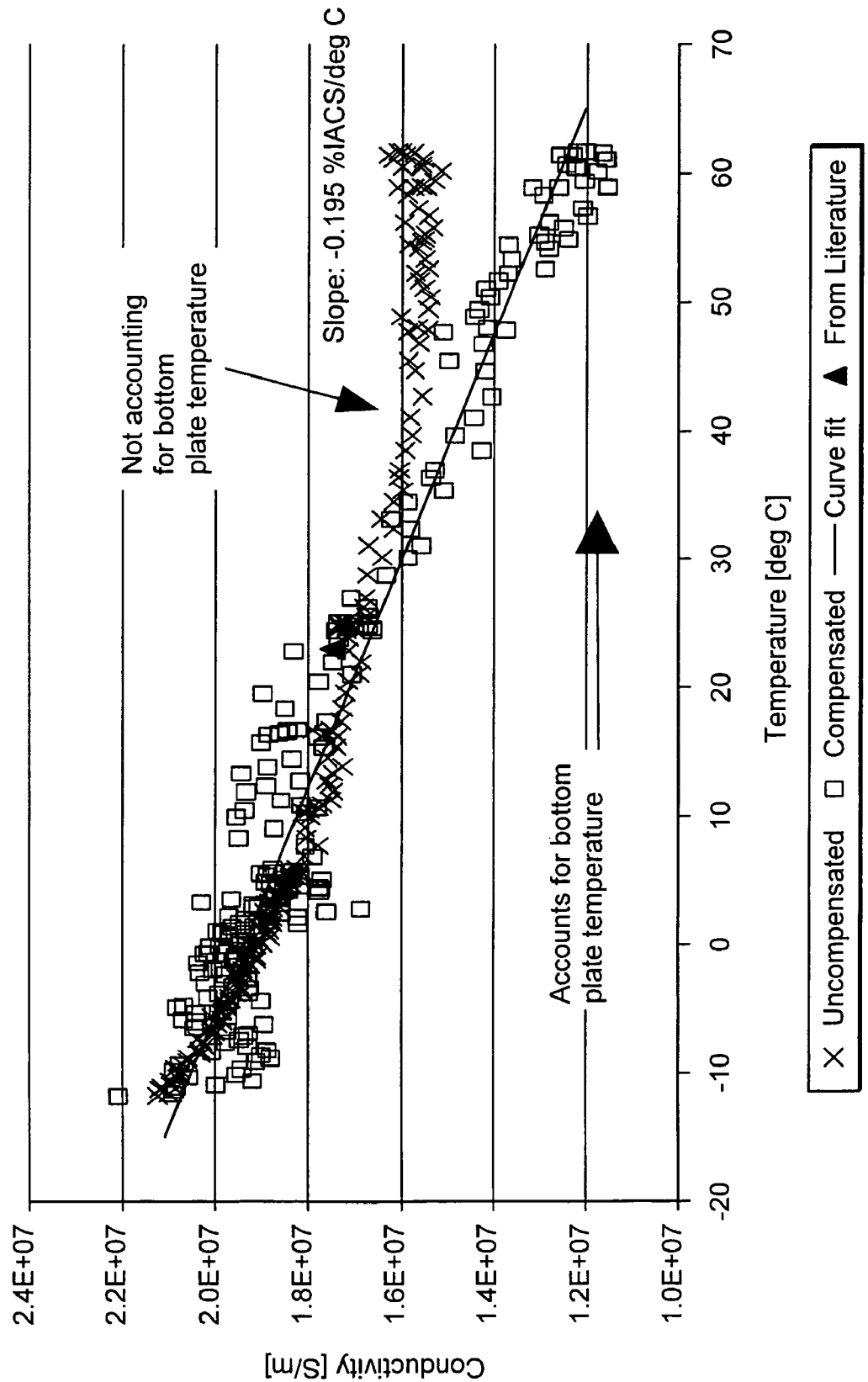
FIG. 15 illustrates the top plate conductivity as a function of temperature with and without compensation for changes in the conductivity of the bottom plate, which is between the top plate and the sensor.

One example application using a GMR sensor is for monitoring properties through intermediate layers of metal. In this case, the absolute electrical properties are measured through thick metal plates and then related to other physical properties of interest. FIG. 14 shows one such layered geometry, with a low frequency (100 Hz) measurement used to remotely monitor the temperature dependent conductivity variation of an aluminum plate through a 0.25-in. thick aluminum plate. The thickness of the upper plate (remote from the sensor), the conductivity and thickness of the bottom plate (near the sensor), as well as its lift-off (proximity) from the sensor windings, are incorporated in the model used to generate the appropriate measurement grids. The two unknown properties are the conductivity of the upper plate and the thickness of the thermally insulating nonconducting spacer between the two plates, which also varied significantly with the temperature of the upper plate. The ability to measure the two unknown parameters independently is demonstrated by taking measurements at room temperature with spacers of varying thickness and demonstrating that the data follow a constant-conductivity line in the grid. To verify and record the actual plate temperatures, thermocouples were attached to both metal plates. The top plate was initially chilled and then gradually heated with a hot air gun. The data of FIG. 15 shows that both the conductivity and spacer thickness are affected by the plate temperature.

In this experiment, the temperature of the bottom plate also increased, despite the thermal insulation. Ignoring this effect yields the plot in FIG. 15 with cross symbols. To compensate for the temperature variation of the bottom plate, data were also taken at 10 kHz simultaneous with the 100 Hz measurement. At this higher frequency the bottom plate appears infinitely thick since it is more than several skin depths thick and a simple conductivity/lift-off grid can be used to independently determine the bottom plate's conductivity. Once this value is obtained, it can be used in the estimation of the upper plate conductivity via a three-dimensional measurement grid, called a grid lattice. Using this method, the data shown with squares in FIG. 15 are obtained. As expected, it follows a linear relationship over this temperature range.

Figure 16:
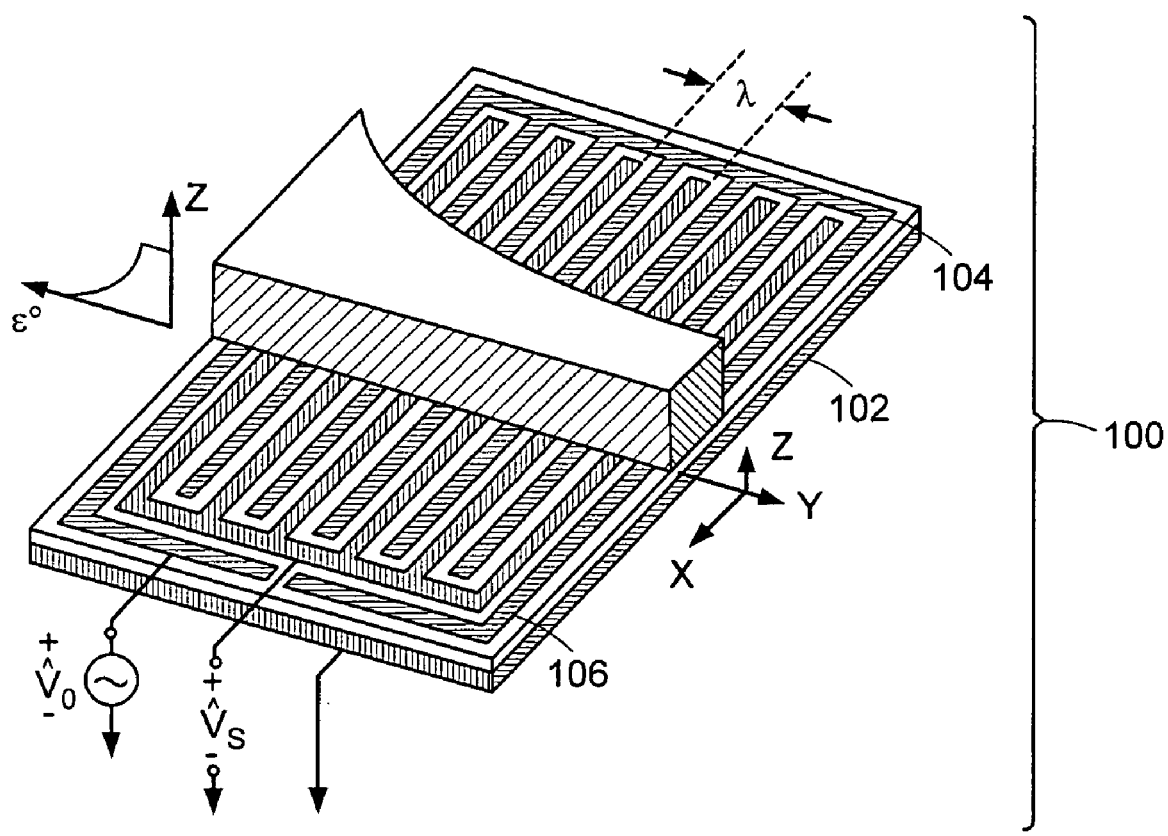
FIG. 16 is a representative single wavelength interdigitated electrode dielectrometer with spatially periodic driven and sensing electrodes of wavelength $\lambda$ that can measure dielectric properties of the adjacent material.

A variety of sensors can be used to monitor the material condition. For example, for insulating or weakly conducting materials such as fiberglass composites, capacitive or dielectric sensors can be used. The sensors are the electromagnetic dual to the inductive sensors, with electric fields taking the place of magnetic fields for inspecting the materials. A representative single sided sensor geometry is shown in FIG. 16. The application of a sinusoidally varying potential of complex magnitude v and angular frequency $\omega=2\pi f$ results in the flow of a terminal current with complex amplitude I, whose magnitude and phase is dependent on the complex permittivity of the material. The capacitive sensor 100 in one preferred embodiment of the invention has interdigitated electrodes as presented in U.S. Pat. Nos. 4,814,690 and 6,380,747 and in U.S. patent application Ser. No. 10/040,797, filed Jan. 7, 2002, and Ser. No. 10/225,406, filed Aug. 20, 2002, the entire teachings of which are hereby incorporated by reference. This sensor 102 utilizes a pair of interdigitated electrodes 104 and 106 to produce a spatially periodic electric field. The electrodes are adjacent to the material of interest with an insulating substrate and a ground plane on the other side of the substrate. One of the two electrodes, 104, is driven with a sinusoidally varying voltage, $v_D$, while the other, 106, is connected to a high-impedance buffer used to measure the magnitude and phase of the floating potential, $v_s$. The periodicity of the electrode structure is denoted by the spatial wavelength $\lambda=2\pi/k$, where k is the wavenumber.

While this invention has been particularly shown and described with references to preferred embodiments thereof, it will be understood by those skilled in the art that various changes in form and details may be made therein without departing from the scope of the invention encompassed by the appended claims.

References incorporated herein by reference in their entirety:
1. DOE Phase II Proposal, titled "Intelligent Probes for Enhanced Non-Destructive Determination of Degradation in Hot-Gas-Path Components," Topic #44c, dated Mar. 23, 2002.
2. NASA Phase II Proposal, titled "Shaped Field Giant Magnetoresisitive Sensor Arrays for Materials Testing," Topic #01-II A1.05-8767, dated May 2, 2002
3. Final Report submitted to NASA, titled "Shaped Field Giant Magnetoresisitive Sensor Arrays for Materials Testing," dated May 3, 2002.
4. Technical paper titled "Friction Stir Weld Inspection through Conductivity Imaging using Shaped Field MWM-Arrays," Proceedings of the 6th International Conference on Trends in Welding, Callaway Gardens, Ga.; ASM International, January 2003.
5. Technical paper titled "Remote Temperature and Stress Monitoring Using Low Frequency Inductive Sensing," SPIE NDE/Health Monitoring of Aerospace Materials and Composites, San Diego, Calif., Mar. 2–6, 2003.
6. Technical paper titled "High Temperature Eddy-Current Sensors for Heat Treatment Monitoring," presented at AeroMat, June 2002.

What is claimed is:

1. A method for calibrating a sensor for use in process control, said method comprising:
   disposing an electromagnetic field sensor proximate to a material that has at least one electrical property that varies with a process condition, the electromagnetic sensor being sensitive to the at least one electrical property;
   disposing a material state sensor proximate to a test material, the material state being temperature;
   measuring the material state sensor at two or more different states to calibrate the electromagnetic field sensor response based on a relationship between the electrical property and the material state, using the calibrated electromagnetic sensor response as an input to a process controller; and
   monitoring the relationship between a process condition and the electromagnetic sensor response to detect changes in the relationship between the electrical property and the material state caused by the process, said changes in the relationship being input to a process controller.

2. A method as claimed in claim 1 further comprising controlling the process on a material, the controlling comprising:
   analyzing the electrical property; and
   using the analyzed result to control the process.

3. The method as claimed in claim 2 wherein the electromagnetic sensor is a magnetic field sensor.

4. The method as claimed in claim 3 wherein the electromagnetic sensor is an eddy current sensor.

5. The method as claimed in claim 3 wherein the electromagnetic sensor is an eddy current sensor array.

6. The method as claimed in claim 3 wherein the electromagnetic sensor comprises a giant magnetoresistive sensor.

7. The method as claimed in claim 2 wherein the electromagnetic sensor is an electric field sensor.

8. The method as claimed in claim 2 wherein the electromagnetic sensor is mounted to a surface of a material.

9. The method as claimed in claim 2 wherein the electromagnetic sensor is scanned over a surface of a material.

10. The method as claimed in claim 2 wherein the electrical property is magnetic permeability.

11. The method as claimed in claim 2 wherein the electrical property is electrical conductivity.

12. The method as claimed in claim 2 wherein analyzing the electrical property further comprises:

comparing the monitored property with an estimated property.

13. The method as claimed in claim 2 wherein the process is a heat treatment.

14. The method as claimed in claim 13 further comprising:
monitoring temperature of the material.

15. The method as claimed in claim 14 wherein analyzing the electrical property further comprises:
comparing the monitored property with an estimated property.

16. The method as claimed in claim 2 further comprising:
exposing the electromagnetic sensor to the process condition of a material.

17. The method as claimed in claim 2 further comprising:
exposing the electromagnetic sensor to a different process condition than the material.

18. The method as claimed in claim 17 further comprising:
placing an intermediate material layer between the electromagnetic sensor and the material.

19. The method as claimed in claim 2 further comprising:
monitoring at least one additional property.

20. The method as claimed in claim 19 wherein the at least one additional property is the electromagnetic sensor lift-off.

21. The method as claimed in claim 2 further comprising:
measuring the property at multiple frequencies.

22. The method as claimed in claim 2 wherein the process is fatigue.

23. The method as claimed in claim 2 wherein the process condition is damage.

24. A method as claimed in claim 1 further comprising calibrating an electromagnetic sensor in-situ, said calibration comprising:
using a known relationship between the process condition and the electrical property to determine a calibration coefficient that adjusts the electromagnetic sensor response to provide an electrical property value that corresponds to the process condition.

25. The method as claimed in claim 24 wherein the electromagnetic sensor is an eddy current sensor.

26. The method as claimed in claim 24 wherein the electromagnetic sensor is an eddy current sensor array.

27. The method as claimed in claim 24 wherein the electrical property is electrical conductivity.

28. The method as claimed in claim 24 wherein the process condition is a change in temperature of the material.

29. A method as claimed in claim 1 further comprising determining a relationship between a process condition and an electrical property of a material, said determination comprising:
measuring said electrical property for at least two different process conditions; and
using measured values to determine the relationship between the process condition and the electrical property.

30. The method as claimed in claim 29 wherein the electromagnetic sensor is an eddy current sensor.

31. The method as claimed in claim 29 wherein the electromagnetic sensor is an eddy current sensor array.

32. The method as claimed in claim 29 wherein the electrical property is electrical conductivity.

33. The method as claimed in claim 29 wherein the process comprises changing temperature of the material.

34. The method as claimed in claim 33 wherein the electrical property is electrical conductivity.

35. The method as claimed in claim 34 wherein the relationship between the temperature and the conductivity is linear.

36. The method as claimed in claim 33 wherein measurements used to determine the relationship are performed during an initial heat treatment.

37. The method as claimed in claim 33 further comprising:
controlling the process to minimize divergence of a measured property from a property estimated from said relationship.

* * * * *

UNITED STATES PATENT AND TRADEMARK OFFICE
CERTIFICATE OF CORRECTION

| | |
|---|---|
| PATENT NO. | : 7,095,224 B2 |
| APPLICATION NO. | : 10/762193 |
| DATED | : August 22, 2006 |
| INVENTOR(S) | : Neil J. Goldfine et al. |

It is certified that error appears in the above-identified patent and that said Letters Patent is hereby corrected as shown below:

<u>In Column 13, Claim 22, line 29</u>

Before "is", insert -- condition --.

Signed and Sealed this

Fifth Day of December, 2006

JON W. DUDAS
*Director of the United States Patent and Trademark Office*